United States Patent
Gless, Jr. et al.

[11] Patent Number: 5,869,740
[45] Date of Patent: Feb. 9, 1999

[54] HERBICIDE INTERMEDIATES

[75] Inventors: Richard D. Gless, Jr., Oakland; Nancy Kerlinger, Lafayette, both of Calif.

[73] Assignee: Zeneca Limited, London, England

[21] Appl. No.: 820,997

[22] Filed: Mar. 20, 1997

Related U.S. Application Data

[62] Division of Ser. No. 489,397, Jun. 12, 1995, Pat. No. 5,659,074.

[51] Int. Cl.⁶ .................................................. C07C 51/16
[52] U.S. Cl. ............................................. 562/422; 562/428
[58] Field of Search ..................................... 562/422, 429

[56] References Cited

FOREIGN PATENT DOCUMENTS

90/02731  3/1990  WIPO .

*Primary Examiner*—Paul J. Killos
*Attorney, Agent, or Firm*—Marian T. Thomson

[57] ABSTRACT

Compounds of the formula:

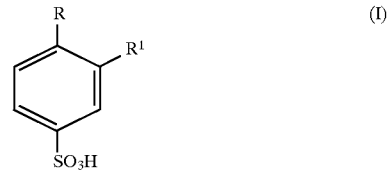

wherein R is $CH_2X$ or $CHX_2$ and X is chloro or bromo and $R^1$ is chloro, bromo or nitro which are useful as intermediates for preparing herbicidal 2-(2'-substituted)-4'-(alkylsulfonyl)benzoyl-1,3-cyclohexanedione compounds.

9 Claims, No Drawings

HERBICIDE INTERMEDIATES

This application is a continuation of application Ser. No. 08/489,397, filed Jun. 12, 1995, now U.S. Pat. No. 5,659,074.

This invention relates to 2-(chloro, bromo or nitro)-4-(sulfo)(halo or dihalo)methylbenzene compounds which are useful as intermediates for the preparation of their corresponding 2-(chloro, bromo or nitro)-4-sulfobenzoic acids.

BACKGROUND OF THE INVENTION

The 2-(chloro, bromo or nitro)-4-(sulfo)(halo or dihalo) methylbenzenes of this invention are useful in the preparation of certain 2-(chloro, bromo or nitro)-4-alkylsulfonyl-benzoyl-1,3-cyclohexanedione herbicides, such as those described in U.S. Pat. No. 4,946,981 and U.S. Pat. No. 5,006,158. The 2-(chloro, bromo or nitro)-4-(sulfo)(halo or dihalo)methylbenzene is oxidized to its corresponding 2-(chloro, bromo or nitro)-4-sulfobenzoic acid. The 2-(chloro, bromo or nitro)-4-sulfobenzoic acid can be used to prepare a 2-(chloro, bromo or nitro)-4-(alkylsulfonyl) benzoic acid, which can then be converted to its acid chloride or cyanide, as described in U.S. Pat. No. 5,008,448. The resulting acid chloride or cyanide can then be reacted with certain 1,3-cyclohexanediones according to the process of U.S. Pat. No. 4,695,673 or U.S. Pat. No. 4,708,127.

SUMMARY OF THE INVENTION

One embodiment of the present invention is a compound having the formula:

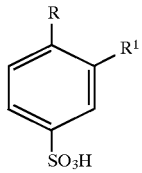

(I)

wherein R is $CH_2X$ or $CHX_2$ and X is Cl or Br and $R^1$ is chloro, bromo or nitro. These compounds are useful in the preparation of 2-(substituted)-4-sulfobenzoic acids and, as such, are useful as intermediates in the preparation of 2-(substituted)-4-(alkylsulfonyl)benzoyl-1,3-cyclohexanedione herbicides.

According to a second embodiment of the invention, there is provided a process for preparing 2-(substituted)-4-sulfobenzoic acids using the intermediate compounds of formula (I).

DETAILED DESCRIPTION OF THE INVENTION

The compounds of formula (I) can be synthesized using the following schematically represented procedure:

SCHEME I

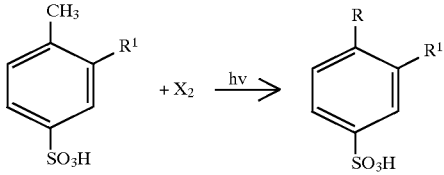

wherein R is $CH_2X$ or $CHX_2$ and X is Cl or Br and $R^1$ is chloro, bromo or nitro; and hv represents ultraviolet light. Preferably, $R^1$ is chloro or nitro.

The reaction of Scheme I is conducted under conditions which will effectuate the halogenation of an alkyl side-chain on the benzene ring. The reaction conditions must lead to the generation of halogen free radicals. One way to accomplish this is through the use of chlorine gas and ultraviolet light. Although chlorine gas is the preferred halogenating agent, bromine is expected to perform the same function.

To prepare the compounds of formula (I), 2-(chloro, bromo or nitro)toluene sulfonic acid is charged into a reaction vessel, such as a round bottom flask, and a solvent is added. Suitable solvents include methylene chloride, chloroform and carbon tetrachloride. Any solvent resistant to halogenation, typically alkyl or aryl polyhalogenated solvents are suitable.

If chlorine is used, chlorine gas is added below the surface of the reaction mixture, in at least a 2 molar excess compared to the toluene sulfonic acid. A 3–4 molar excess of chlorine gas is preferred. The ultraviolet (UV) light source is turned on. The UV light source used can be a conventional sun lamp or other known UV light source, so long as the light source emits light at a wavelength necessary to generate chlorine free radicals. The reaction temperature rises due to the heat generated from the UV light source. The temperature of the reaction depends in part upon the solvent being used, but generally is about 40° to 70° C., and preferably, between 50° to 60° C.

The reaction is run for at least about 1 hour and up to about 6 hours. Preferably, the reaction is run for about 2 to 4 hours. The reaction may be monitored using an appropriate analytical technique, such as nuclear magnetic resonance spectroscopy (NMR), to ascertain the completion of the reaction. Depending on the reaction duration, the relative amounts of 2-(chloro, bromo or nitro)-4-(sulfo) chloromethylbenzene and 2-(chloro, bromo or nitro)-4-(sulfo)dichloromethylbenzene generated can vary. The shorter the reaction duration, the more 2-(substituted)-4-(sulfo)chloromethylbenzene is generated. As described below, either the 2-(chloro, bromo or nitro)-4-(sulfo) dichloromethylbenzene or 2-(chloro, bromo or nitro)-4-(sulfo)chloromethylbenzene may be oxidized to its corresponding 2-(chloro, bromo or nitro)-4-sulfobenzoic acid.

The halomethyl and dihalomethyl moieties of the product of Scheme I may be oxidized to a carboxylic acid moiety, to generate the corresponding 2-(chloro, bromo or nitro)-4-sulfobenzoic acid, using conventional oxidants. These oxidants include sodium hypochlorite, nitric acid and potassium permanganate.

The following examples illustrate the synthesis of representative intermediate compounds of this invention. The structures of these compounds were confirmed by NMR spectroscopy.

EXAMPLE 1

To a 250 mL three-necked round bottom flask equipped with a dry ice condenser thermometer and gas inlet was charged, 10.33 grams of 2-(chloro)toluene sulfonic acid (50 mmol) and 100 mL of chloroform. A sun lamp was turned on and 14 grams of chlorine gas (200 mmol) was added to the flask below the solvent surface. The addition of the chlorine gas was completed over a 4 hour period and the reaction was stirred for an additional hour. The sun lamp maintained the reaction temperature between 50° to 55° C. $^1H$ NMR indicated predominantly 2-(chloro)-4-(sulfo) chloromethylbenzene (~75%) and 2-(chloro)-4-(sulfo) dichloromethylbenzene(~10%).

EXAMPLE 2

To a 250 mL three-necked round bottom flask equipped with a dry ice condenser thermometer and gas inlet was charged about 6.4 grams of 2-(chloro)toluene sulfonic acid (67.3 mmol) and 100 mL of carbon tetrachloride. A sun lamp was turned on and initially about 10 grams of chlorine gas (140 mmol) was added to the flask below the solvent surface. After addition of the chlorine gas (about 1 hour), an $^1$H NMR indicated 30% 2-(chloro)-4-(sulfo)chloromethylbenzene and 70% 2-(chloro)-4-(sulfo)dichloromethylbenzene. The sun lamp maintained the reaction temperature between 60°–65° C. After an additional approximately 15 grams of chlorine gas was added, $^1$H NMR indicated 15% 2-(chloro)-4-(sulfo)chloromethylbenzene and 85% 2-(chloro)-4-(sulfo)dichloromethylbenzene.

EXAMPLE 3

To a 250 mL three-necked round bottom equipped with a condenser and thermometer was charged 7.5 g of 2-(chloro)-4-(sulfo)chloromethylbenzene (25 mmol) and 50 mL of sodium hypochlorite (12.5% solution, 84 mmol). A precipitate formed and 2 g of aqueous sodium hydroxide solution (50% solution, 25 mmol) was added.

The solution was refluxed for 5 hours, then an additional 50 mL of sodium hypochlorite (12.5% solution, 84 mmol) was added. The solution was refluxed an additional 4 hours. The solution was allowed to cool to 40° C. and 20 mL of hydrochloric acid (240 mmol) was added which resulted in the benzoic acid product precipitating. The precipitate was filtered and collected. The collected product, namely 2-(chloro)-4-sulfobenzoic acid was dried and the structure confirmed by nuclear magnetic resonance spectroscopy.

Although the invention has been described with reference to preferred embodiments and particular examples thereof, the scope of the present invention is not limited to those described embodiments. As will be apparent to persons skilled in the art, modifications and adaptations to the above-described invention can be made without departing from the spirit and scope of the invention, which is defined and circumscribed by the appended claims.

What is claimed is:
1. A process of making a compound of the formula

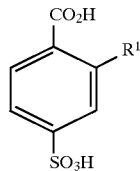

comprising reacting at least a molar equivalent of an oxidant with a molar equivalent of a compound of the formula

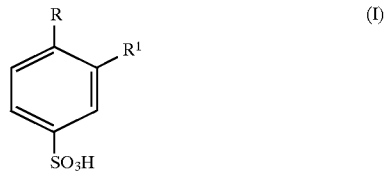

wherein R is $CH_2X$ or $CHX_2$ and X is chloro and $R^1$ is chloro, bromo or nitro.
2. A process according to claim 1, wherein $R^1$ is chloro.
3. A process according to claim 1, wherein $R^1$ is nitro.
4. A process according to claim 1, wherein R is $CH_2Cl$.
5. A process according to claim 1, wherein R is $CHCl_2$.
6. A process according to claim 1, wherein said oxidant is sodium hypochlorite.
7. A process according to claim 1, wherein said oxidant is nitric acid.
8. A process according to claim 1, wherein said oxidant is potassium permanganate.
9. A process according to claim 1, further comprising the initial step of preparing a compound of formula (I) by reacting a compound of the formula:

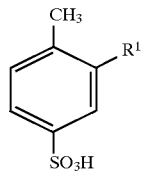

with at least a 2 molar excess of chlorine gas in the presence of ultraviolet light.

* * * * *